United States Patent
Milad et al.

(10) Patent No.: US 11,571,499 B2
(45) Date of Patent: Feb. 7, 2023

(54) DIALYSIS MACHINE

(71) Applicant: QUANTA DIALYSIS TECHNOLOGIES, LTD., Warwickshire (GB)

(72) Inventors: John Milad, Warwickshire (GB); Clive Buckberry, Warwickshire (GB); Mark Wallace, Warwickshire (GB)

(73) Assignee: QUANTA DIALYSIS TECHNOLOGIES LTD., Warwickshire (GB)

( * ) Notice: Subject to any disclaimer, the term of this patent is extended or adjusted under 35 U.S.C. 154(b) by 582 days.

(21) Appl. No.: 16/066,269

(22) PCT Filed: Dec. 9, 2016

(86) PCT No.: PCT/GB2016/053888
§ 371 (c)(1),
(2) Date: Jun. 26, 2018

(87) PCT Pub. No.: WO2017/115069
PCT Pub. Date: Jul. 6, 2017

(65) Prior Publication Data
US 2020/0276372 A1    Sep. 3, 2020

(30) Foreign Application Priority Data

Dec. 30, 2015 (GB) .................... 1523104

(51) Int. Cl.
*A61M 1/14* (2006.01)
*A61M 1/16* (2006.01)

(52) U.S. Cl.
CPC ............ *A61M 1/14* (2013.01); *A61M 1/1621* (2014.02); *A61M 1/1605* (2014.02);
(Continued)

(58) Field of Classification Search
CPC .... A61M 1/14; A61M 1/1621; A61M 1/1605; A61M 1/1607; A61M 1/1609;
(Continued)

(56) References Cited

U.S. PATENT DOCUMENTS 2,696,173 A    12/1954   Thormod
3,338,171 A    8/1967    Conklin et al.
(Continued)

FOREIGN PATENT DOCUMENTS

CA    81430 S        8/1997
DE    10024447 A1    11/2001
(Continued)

OTHER PUBLICATIONS

Huarui He, Mark A. Mortellaro, Marc J. P. Leiner, Robert J. Fraatz, and James K. Tusa Journal of the American Chemical Society 2003 125 (6), 1468-1469 DOI: 10.1021/ja0284761 (Year: 2003).*
(Continued)

*Primary Examiner* — Bradley R Spies
*Assistant Examiner* — Jeannie McDermott
(74) *Attorney, Agent, or Firm* — Cooley LLP

(57) ABSTRACT

A hemodialysis machine comprising a fluid pathway for delivering a dialysate solution, wherein the fluid pathway comprises a pre-dialysis pathway and a post-dialysis pathway, a dialyser for dialysing patient's blood using the dialysate solution, the dialyser connected between the pre-dialysis pathway and the post-dialysis pathway, a first sensor system configured to sense a characteristic of the dialysate solution at a first location on the pre-dialysis pathway, a second sensor system configured to sense a characteristic of the dialysate solution at a second location on the post-dialysis pathway, and a control system configured to make a comparative analysis of the measurements taken by the
(Continued)

first sensor and the second sensor for monitoring the composition of the dialysate solution.

31 Claims, 6 Drawing Sheets

(52) U.S. Cl.
CPC ......... *A61M 1/1607* (2014.02); *A61M 1/1609* (2014.02); *A61M 2205/12* (2013.01); *A61M 2205/3306* (2013.01); *A61M 2205/3375* (2013.01)

(58) Field of Classification Search
CPC ...... A61M 2205/12; A61M 2205/3306; A61M 2205/3375
See application file for complete search history.

(56) References Cited

U.S. PATENT DOCUMENTS

| | | |
|---|---|---|
| 3,468,261 A | 9/1969 | Schmierer |
| 3,605,566 A | 9/1971 | Vetter |
| 3,606,592 A | 9/1971 | Madurski et al. |
| 3,753,493 A | 8/1973 | Mellor |
| 3,774,762 A | 11/1973 | Lichtenstein |
| 3,807,906 A | 4/1974 | Breit |
| 3,921,622 A | 11/1975 | Cole |
| 3,972,320 A | 8/1976 | Kalman |
| 4,070,725 A | 1/1978 | Austin et al. |
| 4,142,845 A | 3/1979 | Lepp et al. |
| 4,161,264 A | 7/1979 | Malmgren |
| 4,205,686 A | 6/1980 | Harris et al. |
| 4,353,990 A | 10/1982 | Manske et al. |
| 4,366,061 A | 12/1982 | Papanek et al. |
| 4,368,261 A | 1/1983 | Klose et al. |
| 4,370,983 A | 2/1983 | Lichtenstein |
| 4,430,048 A | 2/1984 | Fritsch |
| 4,494,912 A | 1/1985 | Pauliukonis |
| D277,991 S | 3/1985 | Becker |
| 4,534,755 A | 8/1985 | Calvert et al. |
| 4,534,756 A | 8/1985 | Nelson |
| 4,546,669 A | 10/1985 | Fischer et al. |
| 4,564,342 A | 1/1986 | Weber et al. |
| 4,599,165 A | 7/1986 | Chevallet |
| 4,648,869 A | 3/1987 | Bobo, Jr. |
| 4,666,598 A | 5/1987 | Heath et al. |
| 4,710,163 A | 12/1987 | Butterfield |
| 4,771,792 A | 9/1988 | Seale |
| 4,828,543 A | 5/1989 | Weiss et al. |
| 4,897,184 A | 1/1990 | Shouldice et al. |
| D308,249 S | 5/1990 | Buckley |
| 4,969,991 A | 11/1990 | Valadez |
| 5,000,664 A | 3/1991 | Lawless et al. |
| 5,012,197 A | 4/1991 | Seiffert et al. |
| 5,032,265 A | 7/1991 | Jha et al. |
| 5,055,198 A | 10/1991 | Shettigar |
| 5,095,910 A | 3/1992 | Powers |
| 5,103,211 A | 4/1992 | Daoud et al. |
| 5,126,831 A | 6/1992 | Nakagawara |
| 5,232,434 A | 8/1993 | Inagaki et al. |
| 5,252,213 A | 10/1993 | Ahmad et al. |
| D341,890 S | 11/1993 | Sievert et al. |
| D344,339 S | 2/1994 | Yoshikawa et al. |
| 5,304,349 A | 4/1994 | Polaschegg |
| D347,896 S | 6/1994 | Dickinson et al. |
| D351,470 S | 10/1994 | Scherer et al. |
| 5,385,540 A | 1/1995 | Abbott et al. |
| 5,421,823 A | 6/1995 | Kamen et al. |
| 5,458,468 A | 10/1995 | Ye et al. |
| 5,476,368 A | 12/1995 | Rabenau et al. |
| 5,476,792 A | 12/1995 | Ezrielev et al. |
| D370,979 S | 6/1996 | Pascale et al. |
| 5,558,347 A | 9/1996 | Nicholson |
| 5,586,872 A | 12/1996 | Skobelev et al. |
| 5,586,873 A | 12/1996 | Novak et al. |
| 5,591,344 A * | 1/1997 | Kenley ................. A61L 2/04 210/636 |
| 5,643,201 A | 7/1997 | Peabody et al. |
| 5,650,071 A | 7/1997 | Brugger et al. |
| 5,653,456 A | 8/1997 | Mough |
| 5,658,456 A | 8/1997 | Kenley et al. |
| 5,665,307 A | 9/1997 | Kirschner et al. |
| 5,727,550 A | 3/1998 | Montecalvo |
| D395,085 S | 6/1998 | Kenley et al. |
| 5,788,851 A | 8/1998 | Kenley et al. |
| 5,807,322 A | 9/1998 | Lindsey et al. |
| 5,882,300 A | 3/1999 | Malinouskas et al. |
| 5,948,247 A | 9/1999 | Gillerfalk et al. |
| 5,957,670 A | 9/1999 | Duncan et al. |
| 5,995,910 A | 11/1999 | Discenzo |
| 6,077,443 A | 6/2000 | Goldau |
| 6,126,831 A | 10/2000 | Goldau et al. |
| 6,132,378 A | 10/2000 | Marino |
| 6,143,181 A | 11/2000 | Falkvall et al. |
| 6,153,102 A | 11/2000 | Kenley et al. |
| 6,216,029 B1 | 4/2001 | Paltieli |
| 6,218,329 B1 | 4/2001 | Singh et al. |
| 6,251,279 B1 | 6/2001 | Peterson et al. |
| 6,261,065 B1 | 7/2001 | Nayak et al. |
| 6,303,036 B1 | 10/2001 | Collins et al. |
| 6,382,923 B1 | 5/2002 | Gray |
| 6,514,462 B1 | 2/2003 | Simons |
| 6,558,347 B1 | 5/2003 | Jhuboo et al. |
| 6,582,206 B2 | 6/2003 | Schluecker |
| 6,626,832 B1 | 9/2003 | Paltieli et al. |
| 6,626,878 B1 | 9/2003 | Leisner et al. |
| 6,645,176 B1 | 11/2003 | Christenson et al. |
| 6,663,829 B1 | 12/2003 | Kjellstrand |
| 6,733,476 B2 | 5/2004 | Christenson et al. |
| 6,743,204 B2 | 6/2004 | Christenson et al. |
| 6,801,646 B1 | 10/2004 | Pena et al. |
| 6,814,547 B2 | 11/2004 | Childers et al. |
| 6,967,002 B1 | 11/2005 | Edgson et al. |
| 7,040,142 B2 | 5/2006 | Burbank |
| 7,107,837 B2 | 9/2006 | Lauman et al. |
| 7,153,286 B2 | 12/2006 | Busby et al. |
| 7,220,358 B2 | 5/2007 | Schacht et al. |
| 7,284,964 B2 | 10/2007 | McDowell et al. |
| 7,383,721 B2 | 6/2008 | Parsons et al. |
| 7,434,312 B2 | 10/2008 | Christenson et al. |
| 7,494,590 B2 | 2/2009 | Felding et al. |
| 7,604,398 B1 | 10/2009 | Akers et al. |
| 7,648,627 B2 | 1/2010 | Beden et al. |
| 7,857,976 B2 | 12/2010 | Bissler et al. |
| 7,874,999 B2 | 1/2011 | Busby |
| 7,896,197 B2 | 3/2011 | Furey et al. |
| D641,882 S | 7/2011 | Hickey et al. |
| 8,114,043 B2 | 2/2012 | Muller |
| 8,132,388 B2 | 3/2012 | Nagy et al. |
| 8,137,184 B2 | 3/2012 | Ajiro et al. |
| 8,137,300 B2 | 3/2012 | Han et al. |
| 8,167,431 B2 | 5/2012 | DeCusatis et al. |
| 8,187,184 B2 | 5/2012 | Muller et al. |
| 8,192,388 B2 | 6/2012 | Hogard |
| 8,197,431 B2 | 6/2012 | Bennison |
| 8,221,320 B2 | 7/2012 | Bouton |
| 8,348,850 B2 | 1/2013 | Frinak et al. |
| 8,360,977 B2 | 1/2013 | Marttila et al. |
| 8,529,490 B2 | 9/2013 | Wariar et al. |
| 8,535,522 B2 | 9/2013 | Fulkerson et al. |
| 8,535,525 B2 | 9/2013 | Heyes et al. |
| D693,469 S | 11/2013 | Chung et al. |
| 8,597,505 B2 | 12/2013 | Fulkerson et al. |
| D702,842 S | 4/2014 | Hyde et al. |
| 8,685,244 B2 | 4/2014 | Heyes et al. |
| 8,696,571 B2 | 4/2014 | Marttila et al. |
| 8,708,908 B2 | 4/2014 | Bouton |
| 8,708,946 B2 | 4/2014 | Han et al. |
| D705,432 S | 5/2014 | Lura et al. |
| 8,798,908 B2 | 8/2014 | Bourdeaut |
| 8,801,646 B2 | 8/2014 | Han et al. |
| D714,454 S | 9/2014 | Amemiya et al. |
| D714,946 S | 10/2014 | Lura et al. |

(56) References Cited

U.S. PATENT DOCUMENTS

| | | |
|---|---|---|
| 8,926,544 B2 | 1/2015 | Hogard |
| D724,740 S | 3/2015 | Collins et al. |
| 8,974,394 B2 | 3/2015 | Frinak et al. |
| 9,011,334 B2 | 4/2015 | Bouton |
| D735,868 S | 8/2015 | Mareguddi et al. |
| 9,220,825 B2 | 12/2015 | Buckberry |
| D781,410 S | 3/2017 | Ritter et al. |
| 9,744,285 B2 | 8/2017 | Heyes et al. |
| 9,833,553 B2 | 12/2017 | Higgitt et al. |
| 10,456,516 B2 | 10/2019 | Heyes et al. |
| D867,597 S | 11/2019 | Bauer et al. |
| 10,543,305 B2 | 1/2020 | Buckberry et al. |
| D879,967 S | 3/2020 | Verguldi et al. |
| D907,211 S | 1/2021 | Spurling |
| 10,881,775 B2 | 1/2021 | Wallace |
| 10,960,120 B2 | 3/2021 | Wallace et al. |
| D924,410 S | 7/2021 | Mendoza et al. |
| D938,046 S | 12/2021 | Gupta et al. |
| 11,365,728 B2 | 6/2022 | Westenbrink |
| 2003/0217962 A1 | 11/2003 | Childers et al. |
| 2004/0195157 A1 | 10/2004 | Mullins et al. |
| 2004/0206703 A1 | 10/2004 | Bosetto et al. |
| 2004/0215129 A1 | 10/2004 | Edgson et al. |
| 2004/0223857 A1 | 11/2004 | Kline |
| 2005/0020961 A1 | 1/2005 | Burbank et al. |
| 2005/0205476 A1 | 9/2005 | Chevallet et al. |
| 2005/0209547 A1 | 9/2005 | Burbank et al. |
| 2005/0234384 A1 | 10/2005 | Westberg et al. |
| 2006/0121623 A1* | 6/2006 | He .................... G01N 33/84 |
| | | 436/163 |
| 2007/0083193 A1 | 4/2007 | Werneth et al. |
| 2008/0006089 A1 | 1/2008 | Adnan et al. |
| 2008/0283096 A1 | 11/2008 | Scheringer et al. |
| 2009/0007642 A1 | 1/2009 | Busby et al. |
| 2009/0009290 A1 | 1/2009 | Kneip et al. |
| 2009/0012450 A1 | 1/2009 | Shah et al. |
| 2009/0012452 A1 | 1/2009 | Slepicka et al. |
| 2009/0012457 A1 | 1/2009 | Childers et al. |
| 2009/0101550 A1* | 4/2009 | Muller ................ A61M 1/3643 |
| | | 210/87 |
| 2009/0211975 A1 | 8/2009 | Brugger et al. |
| 2009/0230043 A1 | 9/2009 | Heyes et al. |
| 2010/0043694 A1 | 2/2010 | Patel |
| 2010/0045471 A1 | 2/2010 | Meyers |
| 2010/0089807 A1 | 4/2010 | Heyes et al. |
| 2010/0139254 A1 | 6/2010 | Sebestyen et al. |
| 2010/0263687 A1 | 10/2010 | Braun et al. |
| 2011/0009797 A1 | 1/2011 | Kelly et al. |
| 2011/0034850 A1 | 2/2011 | Jonsson |
| 2011/0132838 A1 | 6/2011 | Curtis et al. |
| 2011/0168614 A1 | 7/2011 | Pouchoulin et al. |
| 2012/0164022 A1 | 6/2012 | Muginstein et al. |
| 2012/0269907 A1 | 10/2012 | Coates |
| 2012/0276549 A1* | 11/2012 | Cunningham ......... B82Y 15/00 |
| | | 435/7.1 |
| 2012/0292237 A1* | 11/2012 | Heyes .................... B01D 63/06 |
| | | 210/101 |
| 2012/0308431 A1 | 12/2012 | Kotsos et al. |
| 2013/0037465 A1 | 2/2013 | Heyes et al. |
| 2013/0056419 A1 | 3/2013 | Curtis |
| 2013/0153495 A1 | 6/2013 | Kelly et al. |
| 2013/0199998 A1 | 8/2013 | Kelly et al. |
| 2013/0274642 A1* | 10/2013 | Soykan .................. A61B 5/0452 |
| | | 604/5.01 |
| 2014/0224736 A1 | 8/2014 | Heide |
| 2014/0251885 A1 | 9/2014 | Heyes |
| 2014/0271106 A1 | 9/2014 | Alessandro et al. |
| 2014/0299544 A1 | 10/2014 | Wilt et al. |
| 2015/0027951 A1 | 1/2015 | Wallace et al. |
| 2015/0076053 A1 | 3/2015 | Higgitt et al. |
| 2015/0112119 A1 | 4/2015 | Buckberry |
| 2015/0129481 A1 | 5/2015 | Higgitt et al. |
| 2015/0238673 A1 | 8/2015 | Gerber et al. |
| 2015/0258263 A1 | 9/2015 | Hogard |
| 2015/0352269 A1* | 12/2015 | Gerber ..................... A61M 1/16 |
| | | 210/639 |
| 2015/0359954 A1 | 12/2015 | Gerber et al. |
| 2016/0045656 A1* | 2/2016 | Buckberry .......... A61M 1/1656 |
| | | 210/91 |
| 2016/0051743 A1 | 2/2016 | Buckberry |
| 2016/0058933 A1* | 3/2016 | Ballantyne .......... A61M 1/1658 |
| | | 210/85 |
| 2016/0076535 A1 | 3/2016 | Clifton et al. |
| 2016/0077644 A1 | 3/2016 | Ritter et al. |
| 2017/0056576 A1 | 3/2017 | Doyle et al. |
| 2017/0167983 A1* | 6/2017 | Klomp ................ G01N 21/718 |
| 2017/0252498 A1 | 9/2017 | Heyes et al. |
| 2017/0296730 A1 | 10/2017 | Soto et al. |
| 2018/0133391 A1 | 5/2018 | Heyes et al. |
| 2018/0154059 A1 | 6/2018 | Heyes et al. |
| 2018/0193545 A1 | 7/2018 | Crnkovich et al. |
| 2018/0344915 A1 | 12/2018 | Wallace |
| 2019/0001042 A1 | 1/2019 | Buckberry |
| 2019/0015577 A1 | 1/2019 | Garrido et al. |
| 2019/0024654 A1 | 1/2019 | May et al. |
| 2019/0358381 A1 | 11/2019 | Westenbrink |
| 2019/0374698 A1 | 12/2019 | Buckberry et al. |
| 2019/0376504 A1 | 12/2019 | Westenbrink |
| 2019/0385434 A1 | 12/2019 | Yuds et al. |
| 2020/0030515 A1* | 1/2020 | Merchant ............ A61M 1/3609 |
| 2020/0075159 A1 | 3/2020 | Bardorz et al. |
| 2020/0268958 A1 | 8/2020 | Heyes et al. |
| 2020/0330671 A1 | 10/2020 | Buckberry et al. |
| 2021/0110920 A1 | 4/2021 | Heyes et al. |
| 2022/0001087 A1 | 1/2022 | Heyes et al. |
| 2022/0160943 A9 | 5/2022 | Buckberry et al. |
| 2022/0241480 A1 | 8/2022 | Fincham |
| 2022/0241573 A1 | 8/2022 | Fincham |

FOREIGN PATENT DOCUMENTS

| | | |
|---|---|---|
| EM | EU0043757640001 | 10/2017 |
| EM | EU0043757640002 | 10/2017 |
| EM | EU0079551250002 | 6/2020 |
| EP | 0165751 A2 | 12/1985 |
| EP | 0754468 A2 | 1/1997 |
| EP | 2219703 A1 | 8/2010 |
| EP | 2955512 A1 | 12/2015 |
| FR | 2310136 A1 | 12/1976 |
| GB | 90079551250001 | 5/2020 |
| GB | 90079551250002 | 5/2020 |
| JP | H04266740 | 9/1992 |
| JP | H06261872 | 9/1994 |
| JP | H07174659 A | 7/1995 |
| JP | 2000/130334 | 5/2000 |
| JP | 1645323 S | 11/2020 |
| WO | WO 81/01800 | 7/1981 |
| WO | WO-9100113 A2 | 1/1991 |
| WO | WO-9116542 A1 | 10/1991 |
| WO | WO 95/06205 | 3/1995 |
| WO | WO 95/25893 | 9/1995 |
| WO | WO-9625214 A1 | 8/1996 |
| WO | WO-9710013 A1 | 3/1997 |
| WO | WO-9728368 A2 | 8/1997 |
| WO | WO-9929356 A1 | 6/1999 |
| WO | WO 2000/006217 | 2/2000 |
| WO | WO-0057935 A1 | 10/2000 |
| WO | WO-02066833 A1 | 8/2002 |
| WO | WO-02081917 A1 | 10/2002 |
| WO | WO 2003/101510 | 12/2003 |
| WO | WO-2005044339 A2 | 5/2005 |
| WO | WO-2005080794 A1 | 9/2005 |
| WO | 2006120415 A1 | 11/2006 |
| WO | WO 2006/120417 | 11/2006 |
| WO | WO-2008100671 A1 | 8/2008 |
| WO | WO-2008106191 A2 | 9/2008 |
| WO | WO-2008135245 A1 | 11/2008 |
| WO | WO-2009006489 A2 | 1/2009 |
| WO | WO-2009024333 A1 | 2/2009 |
| WO | WO-2009038834 A1 | 3/2009 |
| WO | WO 2009/061608 | 5/2009 |
| WO | WO-2009127624 A2 | 10/2009 |
| WO | WO-2010089130 A1 | 8/2010 |

(56) References Cited

FOREIGN PATENT DOCUMENTS

| WO | WO-2010146343 A2 | 12/2010 | | |
|---|---|---|---|---|
| WO | WO-2011027118 A1 | 3/2011 | | |
| WO | WO-2011068885 A1 | 6/2011 | | |
| WO | WO-2011105697 A2 | 9/2011 | | |
| WO | WO-2011105698 A2 | 9/2011 | | |
| WO | WO 2013/057109 | 4/2013 | | |
| WO | WO-2013052680 A2 | 4/2013 | | |
| WO | WO 2013/110906 | 8/2013 | | |
| WO | WO 2013/110919 | 8/2013 | | |
| WO | WO 2013/114063 | 8/2013 | | |
| WO | WO-2013121162 A1 * | 8/2013 | .......... | A61M 1/1652 |
| WO | WO-2013121163 A1 | 8/2013 | | |
| WO | WO 2014/072195 | 5/2014 | | |
| WO | WO-2014082855 A1 | 6/2014 | | |
| WO | 2014155121 A2 | 10/2014 | | |
| WO | WO 2015/007596 | 1/2015 | | |
| WO | WO 2015/022537 | 2/2015 | | |
| WO | WO 2016/016870 | 2/2016 | | |
| WO | WO-2017137723 A1 | 8/2017 | | |
| WO | WO-2018115816 A1 | 6/2018 | | |

OTHER PUBLICATIONS

International Search Report and Written Opinon issued for International Application No. PCT/GB2016/053888, dated Feb. 20, 2017.

Kivi, Air Embolism, Healthline, Aug. 20, 2012, p. 1-5.

Ergo-Express Motorized Dialysis Cart, Aug. 14, 2017, youtube.com [online], [site visited Jan. 9, 2022], Available from internet, URL: https://www.youtube.com/watch?v=j4rAXthOmbY (Year: 2017).

Home Dialysis Tescon Aqua Tech, Aug. 1, 2020, youtube.com [online], [site visited Jan. 9, 2022], Available from internet, URL: https://www.youtube.com/watch?v=WLLPZoS_mz4 (Year: 2020).

LH02028 Portable Hemodialysis Machine, date unknown, aliexpress.com [online], [site visited Jan. 4, 2022], Available from internet: https://www.aliexpress.eom/item/1005003324875329.html?randl_currency=USD&_randl shipto=US&src=google&aff_fcid=1003bab3b8db4e93b9ba88522a14cfc1-1641319351626-05232-UneMJZVf&aff fsk-UneMJZVf&aff_platform=aaf&sk=UneMJZVf &aff_trace_key= (Year: 2022).

Medical Hemodialysis Machine, date unknown, aliexpress.com [online], [site visited Jan. 4, 2022], Available from internet: https://www.aliexpress.com/item/1005003445721549.html?_randl_currency=USD&_randl_shipto=US&src=google&aff_fcid=a524f3f9cd9b4976b6b47962f3439d62-1641319166409-02691-UneMJZVf&aff_fsk-UneMJZVf&aff platform-aaf&sk=UneMJZVf &aff_trace_key=a524f 3f9cd9b4976b6b47962f3439d62-1641319166409-02691-UneMJZVf&terminal_id= d0c2cca4b7664d 128cb4801 a9ef03ff2 (Year: 2022).

Millenium HX Portable Dialysis Water System, Jul. 2, 2014, youtube.com [online], [site visited Jan. 10, 2022], Available from internet, URL: https://www.youtube.com/watch?v=IGEbPi2CDsw (Year: 2014).

Portable home dialysis device, Nov. 2, 2017, med-technews.com [online], [site visited Jan. 4, 2022], Available from internet: https://www.med-technews.com/news/portable-home-dialysis-device-to-launch-next-year/ (Year: 2017).

* cited by examiner

DIALYSIS MACHINE

This application is a National Stage Entry entitled to and hereby claiming priority under 35 U.S.C. §§ 365 and 371 to corresponding PCT Application No. PCT/GB2016/053888, filed Dec. 9, 2016 entitled "A Dialysis Machine", which in turn claims priority to G.B. Patent Application No.: 1523104.6, filed Dec. 30, 2015, entitled the same. The disclosures of the above applications are incorporated herein by reference in their entireties.

FIELD OF THE INVENTION

The present invention relates to a dialysis machine.

BACKGROUND OF THE INVENTION

Dialysis is a treatment which replaces the renal function of removing excess fluid and waste products, such as potassium and urea, from blood. The treatment is either employed when renal function has deteriorated to an extent that uremic syndrome becomes a threat to the body's physiology (acute renal failure) or, when a longstanding renal condition impairs the performance of the kidneys (chronic renal failure).

There are two major types of dialysis, namely hemodialysis and peritoneal dialysis. In peritoneal dialysis treatment, a dialysate solution is run through a tube into the peritoneal cavity. The fluid is left in the cavity for a period of time in order to absorb the waste products, and is subsequently removed through the tube for disposal. It is common for patients in the early stages of treatment for a longstanding renal condition to be treated by peritoneal dialysis before progressing to hemodialysis at a later stage. In hemodialysis, the patient's blood is removed from the body by an arterial line and treated by a dialysis machine before being returned to the patient's body by a venous line. The machine passes the blood through a dialyser containing tubes formed from a semi-permeable membrane. On the exterior of the semi-permeable membrane is a dialysate solution. The semi-permeable membrane filters the waste products and excess fluid from the blood into the dialysate solution. The membrane allows the waste and a controlled volume of fluid to permeate into the dialysate solution whilst preventing the loss of larger more desirable molecules, like blood cells and certain proteins and polypeptides.

The action of dialysis across the membrane is achieved primarily by diffusion (the migration of molecules by random motion from a region of higher concentration to a region of lower concentration). Fluid removal (otherwise known as ultrafiltration) is achieved by altering the hydrostatic pressure of the dialysate solution side of the membrane, causing free water to move across the membrane along the pressure gradient. The correction of uremic acidosis of the blood is achieved by use of a bicarbonate buffer. The bicarbonate buffer also allows the correction of the blood bicarbonate level. The dialysate solution consists of a sterilized solution of mineral ions. These ions are contained within an acid buffer which is mixed with the purified water and bicarbonate base prior to delivery to the dialyser.

In use, the dialysate solution may be passed through the dialyser once before being discarded to ensure that the composition of the dialysate solution remains constant. However, this requires up to 120 litres of dialysate solution for each dialysis session. Alternatively, a closed loop fluid path dialysis machine may be used so as to reduce the amount dialysate solution required for a single session down to 6 to 10 litres. The reduced amount of dialysate solution required can be provided in a pre-mixed supply thus removing the requirement to connect the hemodialysis machine to a permanent source of purified water, for example water purified by reverse osmosis from a mains supply. The composition of recirculated dialysate solution needs to be tightly controlled to keep the patient's blood at an optimal composition.

Monitoring of the dialysate solution can be done by a range of means such as temperature and conductivity sensing as well as other methods. Typically, such measurements are taken with respect to an absolute reference point which may result in slight errors or uncertainties in the measurements due to minor differences between the material/solution used to record the absolute reference point and the material/solution used in the dialysis machine.

The present invention seeks to provide an improved hemodialysis machine.

SUMMARY OF THE INVENTION

A first aspect of the invention provides a hemodialysis machine comprising a fluid pathway for delivering a dialysate solution, wherein the fluid pathway comprises a pre-dialysis pathway and a post-dialysis pathway, a dialyser for dialysing patient's blood using the dialysate solution, the dialyser connected between the pre-dialysis pathway and the post-dialysis pathway, a first sensor system configured to sense a characteristic of the dialysate solution at a first location on the pre-dialysis pathway, a second sensor system configured to sense a characteristic of the dialysate solution at a second location on the post-dialysis pathway and a control system configured to make a comparative analysis of the measurements taken by the first sensor and the second sensor for monitoring the composition of the dialysate solution.

Advantageously, this arrangement can be used to measure the concentrations of dialysate, acid, sodium bicarbonate and water in their respective flow paths via comparative measurements without reliance on an absolute reference point. Additionally, this machine is also able to determine if there is a blood leak in any of the flow paths.

Preferably, the hemodialysis machine comprises a removable, mountable cartridge, wherein the cartridge defines the fluid pathway.

Provision of a cartridge as a consumable component, in combination with filtration of dialysate solution, allows for the hemodialysis machine to be optimised for convenient transportation with the patient. This is advantageous as typically a patient is required to be treated either at a medical facility or at home due to the large size of conventional hemodialysis machines. A smaller machine, similar to the size of a conventional desktop computer, would permit a patient to self-dialyse at any convenient location.

Where the machine is provided with a cartridge, the first sensor system preferably comprises a first sensor cell located on the cartridge and the second sensor system comprises a second sensor cell located on the cartridge.

Advantageously, providing the sensor cells on the removable cartridge.

The cartridge may comprise a dialyser outlet and the first sensor cell is located immediately upstream of said dialyser outlet.

The cartridge may comprise a dialyser inlet and the second sensor cell is located immediately downstream of said dialyser inlet.

Advantageously, this ensures that the dialysate is analysed at similar points along the flow path regardless of direction of flow of the dialysate. The first and second sensor systems may sense a characteristic of the dialysate solution by passing light through the solution. Alternatively, the first and second sensor systems may sense a characteristic of the dialysate solution by passing ultrasound through the solution.

The cartridge may comprise a cartridge drain outlet and a third sensor cell is located immediately upstream of the cartridge outlet port.

Advantageously, this enables the system to analyse the constituents of the dialysate when the machine is put into bypass mode so as to bypass the sensor cells. This can then be used as reference measurements for each component.

The cartridge may comprise a water inlet port and a fourth sensor cell located immediately downstream of the water inlet port.

Advantageously, this enables the RO water to be analysed when it enters the cartridge. This measurement can then be used as a comparison for the water in the dialysate and can, for example, be used to determine the efficiency of any water treatment/regeneration unit in the hemodialysis machine.

Each sensor cell preferably comprises a window formed in the cartridge.

Advantageously, this arrangement provides a more optically transparent region to reduce attenuation of a signal of a sensor.

The window may comprise a separate plastics material secured to the cartridge.

In that way, one may select the material for the window for each different type of sensor used.

The window may comprise a flexible membrane arranged to minimise unwanted reflections.

Advantageously, the flexible membrane is very thin and so results in greatly reduced attenuation of the sensor signal.

Where the hemodialysis machine comprises a platen and a door and wherein the cartridge is configured to be removably mountable between said platen and door, the door is capable of opening and closing relative to the platen so as to prevent any external light from entering the sensor cells.

Advantageously, this provides a simple way of blocking background light from entering the sensor cells.

Each sensor system may comprise a light source and a detector, wherein each detector is preferably located in the platen.

The light source may be located in the door or in the platen.

Each sensor system may comprise a reflective surface.

Advantageously, this enables reflective absorption spectroscopy to be utilised. This increases the flow path and hence the absorption which increases the overall sensitivity of the sensor. Multiple reflective surfaces in the system could further increase the sensitivity by further increasing the flow path through the fluid being measured.

The reflective surface is preferably provided on the door.

The hemodialysis machine may comprise an optical lever, preferably formed integrally with the cartridge.

At least one of the sensor cells may comprise a functional coating configured to react to the dialysate solution.

Advantageously, functional coatings can react with components of the dialysate solution, such as oxygen, in a measureable way, such as via fluorescence. This can enable the sensor systems to determine absolute quantities of components of the dialysate.

A particulate sensor configured to analyse the size distribution of particulate matter in the dialysate may be provided.

Advantageously, this enables the system to monitor whether there is a build of large particulate matter in the system which may cause blockages in the dialyser.

The hemodialysis machine may contain a fixed volume of dialysate solution.

The cartridge is disposable.

Advantageously, this enables the sensor cells to be disposed of after each use, ensuring that the sensor cells are clean for each session and reduces the need for cleaning processes to be carried out following each session. Furthermore, provision of a disposable cartridge permits the majority of the fluid components of the hemodialysis machine to be disposed of after each use, thus reducing the risk of contamination of infection occurring.

According to a second aspect of the invention, there is provided a cartridge for use in a hemodialysis machine, the cartridge defining a fluid pathway for delivering clean dialysate solution to a dialyser via a pre-dialysis pathway and for receiving used dialysate solution from the dialyser via a post dialysis pathway, the cartridge defining a sensor cell in the pre-dialysis pathway and a sensor cell in the post dialysis pathway.

BRIEF DESCRIPTION OF THE DRAWINGS

Embodiments of the invention will now be described with reference to the accompanying drawings, in which.

DETAILED DESCRIPTION OF EMBODIMENTS

Figure 1:
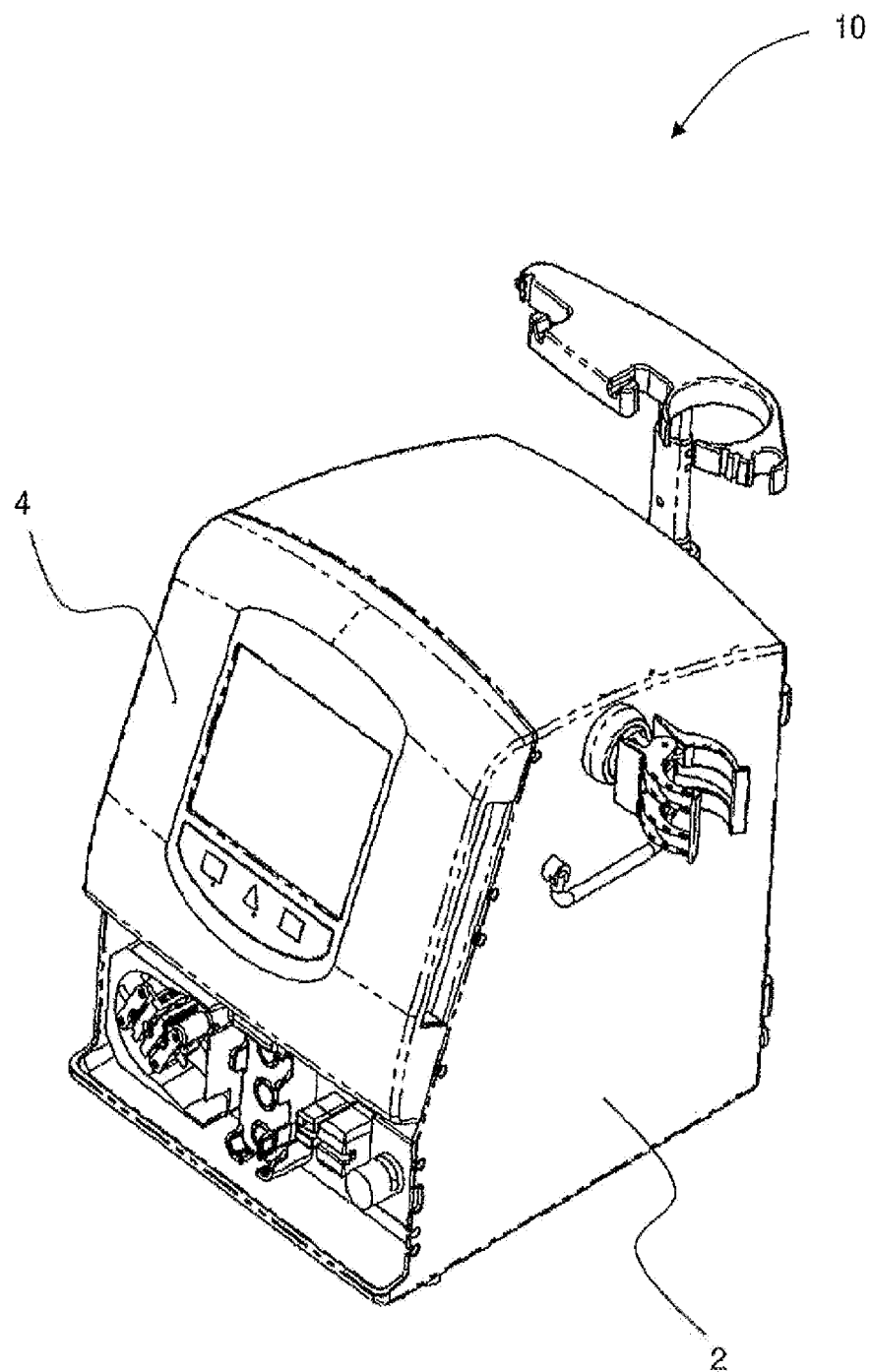
FIG. 1 is an isometric view of a dialysis apparatus including the cartridge according to an embodiment of the present invention.

In FIG. 1, a dialysis apparatus 10 has a body 2 and a hinged door 4. The door 4 is hinged so as to allow a dialysis cartridge 30 (see FIG. 3) to be received between the body 2 and the door 4 before the door is closed to engage the cartridge 30. The body 2 includes a platen provided with pneumatic pumps for operating the cartridge 30 and a series of sensors for sensing a dialysate solution (and constituent components thereof) along a fluid pathway for delivering a dialysate solution, as will be discussed in further detail below. The dialysate solution flows along a pre-dialysis pathway into a dialyser 12 and along a post-dialysis pathway towards a drain outlet 122.

The cartridge 30 has a platen side 31 and a door side 32. The platen side 31 engages the platen on the main body 2 of the machine 10, and the door side 32 engages the door 4 of the machine 10. The cartridge 30 is formed from an acrylic, such as SG-I0, which is moulded in two parts (the machine side and the patient side) before being bonded together. In this way a series of flow paths are formed in the cartridge 30 for carrying dialysate and its constituent parts of water, bicarbonate solution and acid solution. Both the platen side 31 and door side 32 are covered in a clear flexible membrane formed from, for example, DEHP-free PVC which is operable by pneumatic pressure applied to the membrane by a pneumatic compressor in the main body 2.

Figure 2:
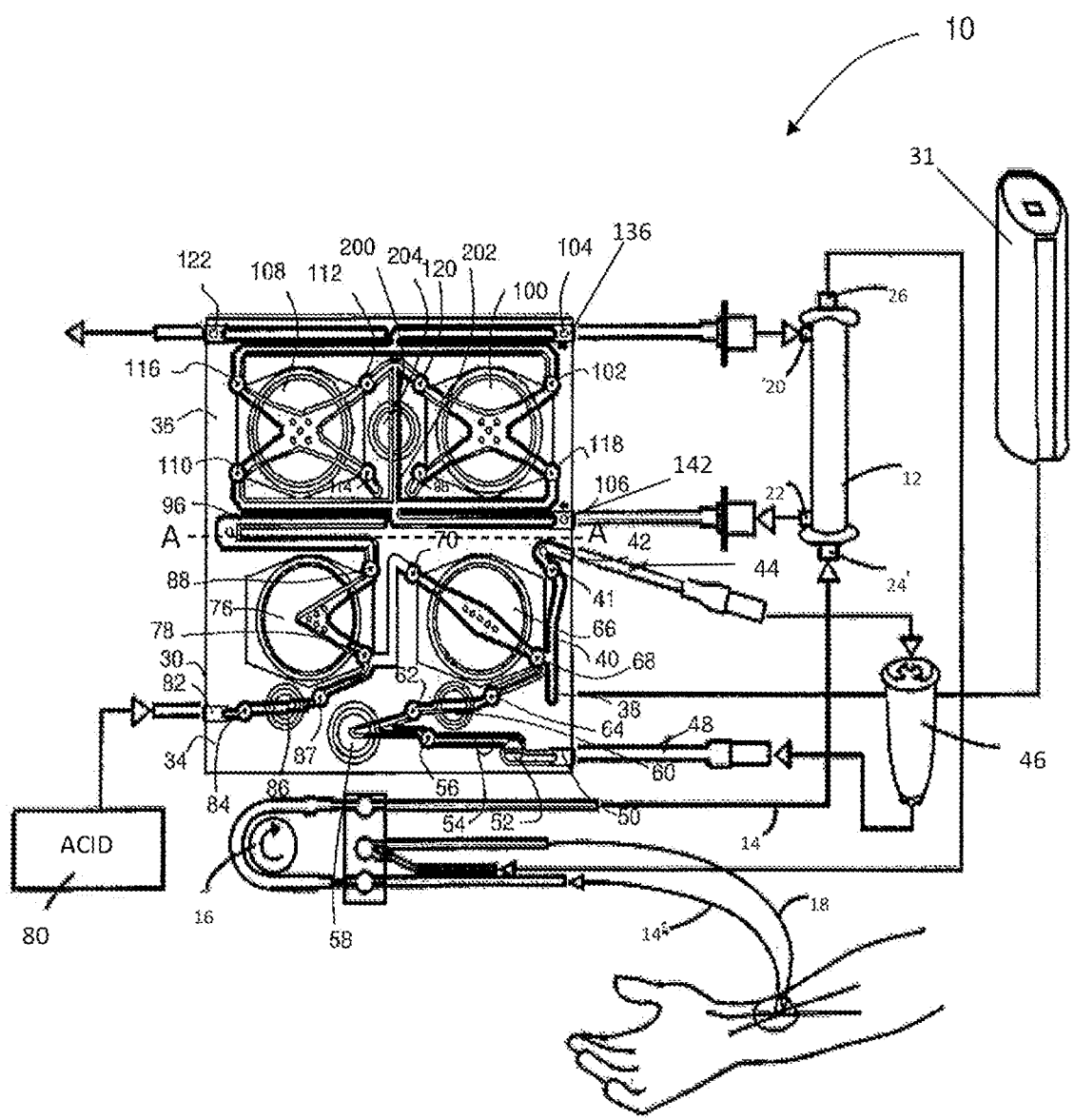
FIG. 2 is a schematic of the dialysis apparatus of FIG. 1 including, inter alia, a dialysis cartridge.

Referring to FIG. 2, a schematic dialysis system, generally referred to at 10, is illustrated. A dialyser 12 receives blood via an arterial line 14 connected to a patient by a vascular access device (not shown for clarity), for example a hollow needle as typically used for drawing blood from a patient. The blood is pumped from the patient to the dialyser 12 by a peristaltic pump 16. The blood passes through the dialyser 12 in a known manner and is returned to the patient via a venous line 18. The dialyser 12 comprises a cylindrical tube closed by opposing ends. A semi-permeable membrane (not shown) is provided within the dialyser tube and separates the patients' blood from a dialysate solution. The membrane extends substantially between the opposing ends of the cylinder. The dialysate solution removes impurities from the patients' blood in a known manner.

The dialyser 12 has an inlet 20 for receiving clean dialysate solution and an outlet 22 for removing spent dialysate solution from the dialyser 12. The dialyser also has an inlet 24 for receiving untreated blood from the peristaltic pump 16 and an outlet 26 for returning processed blood to the patient. The dialyser 12 is typically provided in a substantially upright orientation, in use, with the patient's blood flowing longitudinally through the dialyser 12 from the blood inlet 24 to the blood outlet 26. The dialysate solution inlet 20 and dialysate solution outlet 22 are configured to be orientated substantially orthogonal to the blood inlet 24 and blood outlet 26, and to provide a counterflow. Dialysate solution is circulated through the hemodialysis machine 10 at a fluid flow rate in the region of 400 to 800 ml/min for approximately four hours.

The dialysis system defines a fluid circuit including a cartridge 30 as will now be described. The cartridge 30 is a consumable (i.e. disposable) component within the hemodialysis machine 10 described.

Figure 3:
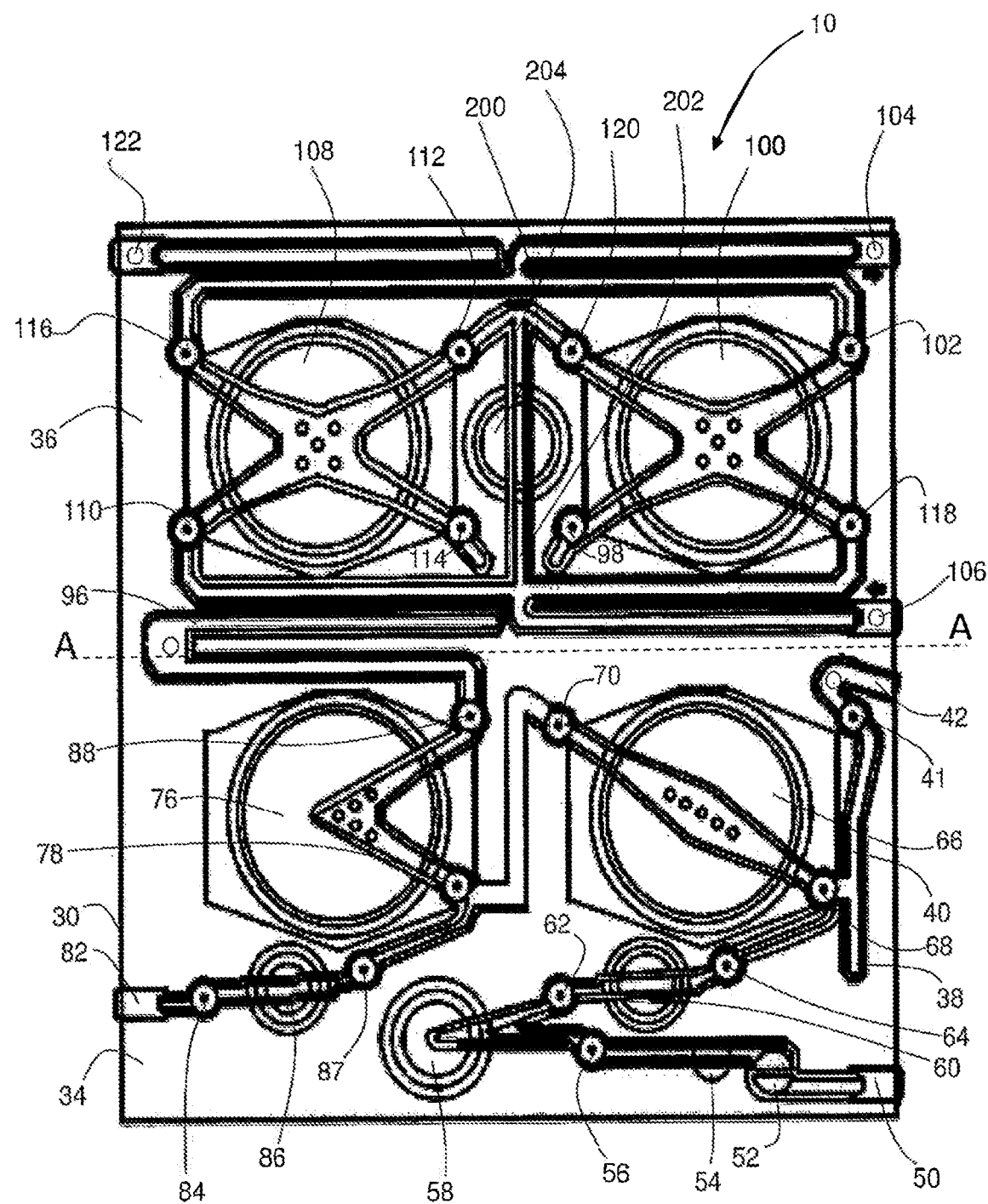
FIG. 3 shows a detailed schematic view of the dialysis cartridge of FIG. 2.

Referring to FIG. 3, the cartridge 30 is illustrated in more detail. The cartridge 30 defines pump chambers which are closed by respective diaphragms, formed from, for example, DEHP-free PVC, to define respective pumps. In this embodiment, each diaphragm is part of a single, common sheet of material applied to the platen side 31 of the cartridge 30. The individual diaphragms are operable by pneumatic pressure or vacuum applied thereto.

A series of flow paths are formed in the cartridge 30 for carrying dialysate solution constituted from water, bicarbonate solution and acid solution. The flow paths are located between the sheet of material closing the machine side 31 of the cartridge 30 and a further sheet of the same material closing the patient side 32 of the cartridge 30.

In use, the variation of pressure applied to the flexible diaphragm of each pump chamber is controlled by conventional valving. A pressure source applies either a positive or negative pneumatic pressure to one side of the diaphragm of each pump chamber, as required, to pump fluid through the fluid paths in the cartridge 30, in a circuit defined by a plurality of valves.

The valves of the cartridge 30 are conventional diaphragm valves defined by respective openings in the cartridge 30 and closed by respective flexible diaphragms. Each valve is operable by applying a negative pressure to the diaphragm to open the valve and applying a positive pressure to the diaphragm to close the valve. The diaphragm of each valve is part of the single, common sheet of material applied to the machine side of the cartridge 30. The valves are opened and closed according to a flow control strategy, as will become apparent.

The machine side of the cartridge 30 abuts a pump driver (not shown) comprising a platen having a plurality of recessed surfaces, each recessed surface substantially corresponding in geometry and volume to a pump chamber defined in the cartridge 30. Each recessed surface has a fluid port connectable with a source of positive fluid pressure and, with a source of negative fluid pressure via a valve.

The positive and negative fluid pressure sources include a pressure pump and a vacuum pump respectively. When the valve is operated to allow fluid to flow into a recessed surface from the source of positive fluid pressure, the diaphragm moves into a corresponding pump chamber and any fluid, i.e. dialysate solution, therein is expelled from that pump chamber via the series of flow paths. When the valve is operated to allow fluid to flow out of a recessed surface to the source of negative fluid pressure, the diaphragm is moved away from a pump chamber and into the corresponding recessed surface to permit fluid to be drawn into that pump chamber via the series of flow paths. The surface of the pump chambers and of the platen provide a positive stop for each diaphragm, to prevent overstretching thereof. The positive stop ensures that the volume of fluid drawn into and pumped from the pump chambers is accurately controlled and remains constant during the dialysis session.

The cartridge 30 has two main functions, preparation of dialysate solution and flow balance. Each function is performed by a separate part of the cartridge 30 as illustrated in FIGS. 2 and 3 by the schematic separation of the cartridge 30 into two parts by the line A-A. The dialysate preparation function is performed by one part of the cartridge, generally referred to at 34 and the flow balance function is performed by the other part of the cartridge, generally referred to at 36. The cartridge 30 prepares an accurately mixed homogenous dialysate solution and ensures that the flow of clean dialysate supplied to the dialyser 12 matches (to within clinical tolerances) the volume of spent dialysate drawn from the dialyser 12.

The cartridge 30 is further provided with a plurality of connections to and from the cartridge 30. A first inlet port 38, from hereon referred to as the water inlet port, defined in the machine side of the cartridge 30 receives purified water from a purified water supply 31 such as a reverse osmosis (RO) water supply. A first outlet port 42, from hereon referred to as the water outlet port, defined in an edge of the cartridge 30 directs the purified water to a first dialysate solution constituent which, in the illustrated embodiment, is bicarbonate 46.

A second inlet port 50, from hereon referred to as the bicarbonate inlet port, defined in the same edge of the cartridge 30 as the water outlet port 42 receives purified water mixed with the bicarbonate 46.

A third inlet port 82, from hereon referred to as the acid inlet port, defined in the opposite edge of the cartridge 30 to the water outlet port 42 and bicarbonate inlet port 50 receives a second dialysate solution constituent which, in the illustrated embodiment, is acid 80 and enables the acid 80 to mix with the purified water mixed with bicarbonate 46.

A second outlet port 104, from hereon referred to as the clean dialysate solution outlet port, is defined in the same edge of the cartridge as the water outlet port 42 and the bicarbonate inlet port 50. The clean dialysate outlet port 104 directs clean dialysate solution to the dialyser 12. A fourth inlet port 106, from hereon referred to as the spent dialysate solution inlet port, is defined in the same edge of the cartridge 30 as the water outlet port 42, bicarbonate inlet port 50 and clean dialysate outlet port 104. The spent dialysate solution inlet port 106 receives spent dialysate solution from the dialyser 12.

A third outlet port 122, from hereon referred to as the drain port, is defined in the same edge of the cartridge as the acid inlet port 82. In the illustrated embodiment, the drain port 122 directs spent dialysate solution out of the cartridge 30.

Dialysate Preparation

Dialysate solution is prepared in the cartridge 30 by combining purified water with two dialysate constituents, namely a bicarbonate solution and an acid solution.

Purified water is admitted into the cartridge 30 from a purified water supply 31 via the water inlet port 38. The purified water passes through a channel 40 via a water inlet valve 41, when open, and exits the cartridge 30 at the water outlet port 42. The characteristics of the purified water is measured at water sensor cell 124, which in this embodiment, is located immediately upstream of the water inlet valve 41. By sensor cell, we mean a part configured to allow sensing of material contained therein or passing therethrough. The water sensor cell 124 is described in more detail below. However, it will be appreciated that the water sensor cell 124 may be positioned anywhere between the water inlet 38 and water outlet 42. Positioning the water sensor cell 124 proximate then the water outlet 42 enables the characteristics of the bicarbonate solution to be measured. If the bicarbonate solution is passed back through the bicarbonate cartridge 46 by closing bicarbonate mixing chamber valve 68. From here, the purified water is carried by a tube 44 through a bicarbonate cartridge 46 in a known manner to generate a purified water and bicarbonate solution. The purified water and bicarbonate solution is carried by a tube 48 and re-admitted into the cartridge 30 via the bicarbonate inlet port 50.

The temperature of the bicarbonate solution is measured at sensing port 52 and the bicarbonate solution pressure is measured at sensing port 54. The bicarbonate solution passes through a bicarbonate control valve 56, when open, before entering a bicarbonate solution reservoir 58 having an inlet and an outlet. The bicarbonate control valve 56 is closed when flow therethrough is not required.

A bicarbonate dosing pump chamber 60 having an inlet and an outlet receives the bicarbonate solution from the bicarbonate solution reservoir 58 through a bicarbonate dosing pump inlet valve 62. The bicarbonate dosing pump chamber 60 is closed by a diaphragm to define a bicarbonate dosing pump which, upon actuation of the diaphragm, pumps the bicarbonate solution from the bicarbonate dosing pump 60 to a first mixing pump chamber 66 (bicarbonate pump chamber). The bicarbonate dosing pump 60 has a bicarbonate dosing pump outlet valve 64 which is closed when the bicarbonate dosing pump inlet valve 62 is open. The bicarbonate dosing pump outlet valve 64 is opened to permit bicarbonate solution to be pumped to the bicarbonate pump chamber 66. When the bicarbonate dosing pump outlet valve 64 is open, the bicarbonate dosing pump inlet valve 62 is closed to prevent bicarbonate solution from being pumped back into the bicarbonate solution reservoir 58.

The bicarbonate pump chamber 66 having an inlet and an outlet receives the purified water and bicarbonate solution from the bicarbonate dosing pump 60 via a bicarbonate pump inlet valve 68. The bicarbonate pump inlet valve 68, when open, can also admit purified water into the bicarbonate pump chamber 66 from the water inlet port 38. The bicarbonate pump chamber 66 is closed by a diaphragm to define a pump which, upon actuation of the diaphragm, pumps the bicarbonate solution and purified water therein through a bicarbonate pump outlet valve 70 to a second mixing pump chamber 76 (acid pump).

When the bicarbonate pump inlet valve 68 is open, the bicarbonate pump outlet valve 70 and water outlet valve 41 are closed. When the bicarbonate pump outlet valve 70 is open, the bicarbonate pump inlet valve 68 is closed to prevent the bicarbonate and purified water solution from being pumped back into channel 40. From the bicarbonate pump outlet valve 70, the bicarbonate and purified water solution enters the acid pump chamber 76.

The acid pump chamber 76 having an inlet and an outlet receives the bicarbonate and purified water solution from the bicarbonate pump 66 via an acid pump inlet valve 78. The acid pump inlet valve 78, when open, can also admit an acid solution into the pump chamber 76. The acid pump chamber 76 is closed by a diaphragm to define a pump which, upon actuation of the diaphragm, pumps the acid solution, bicarbonate solution and purified water therein through an acid pump outlet valve 88 to the first flow balance pump chamber 100. When the acid pump inlet valve 78 is open, the acid pump outlet valve 88 is closed. When the acid pump outlet valve 88 is open, the acid pump inlet valve 78 is closed.

The acid solution is admitted into the cartridge 30 from a pre-determined supply of acid 80 via the acid solution inlet port 82. From the acid solution inlet port the acid solution passes through an acid dosing pump chamber 86 via an acid dosing pump inlet valve 84 and an acid dosing pump outlet valve 87. The acid dosing pump outlet valve 87 is closed when the acid dosing pump inlet valve 84 is open. The acid dosing pump inlet valve 84 is closed when the acid dosing pump outlet valve 87 is open.

The dialysate solution exits the acid pump chamber 76 via the acid pump outlet valve 88 and passes through a first dialysate solution sensor cell 130, described in more detail below, which is also known as a pre-flow balancer sensor cell. The sensor cell 130 is located upstream of both the first and second flow balance chambers 100, 108, i.e. prior to the separation of the single channel from the acid pump chamber 79 into two flow paths (one to each balance chamber).

Flow Balance

The flow balance function of the cartridge 30 provides first and second flow balance pump chambers 100, 108, each having two inlets and two outlets to define two independent flow paths therethrough. The first and second flow balance pump chambers 100, 108 are of approximately equal volume. Either the first or second flow balance pump chamber 100, 108 pumps dialysate solution to a dialyser 12 and the other of the first or second flow balance pump chambers 100, 108 pumps dialysate solution from the dialyser 12 to the drain port 122. After every approximately 20 strokes of the first and second flow balance pumps 100, 108, their function is reversed.

From this point onwards, dialysate solution will be referred to as either clean dialysate solution or spent dialysate solution. Clean dialysate solution is intended to mean dialysate solution that is either new dialysate solution or clean dialysate solution that has been treated to remove waste product therefrom. Spent dialysate solution is intended to mean dialysate solution that has passed through the dialyser 12 to remove waste fluids from a patients' blood into the dialysate solution.

Each of the first and second flow balance pump chambers 100, 108 are closed by a diaphragm to define respective pumps. The diaphragm is actuated away from a pump chamber by a negative pressure source to draw a volumetrically measured quantity of dialysate solution into the pump chamber. The diaphragm is actuated toward the pump chamber to pump the fluid therein out of an outlet.

The first flow balance pump chamber 100 has a clean dialysate solution inlet valve 98 for receiving clean dialysate solution from the acid pump 76 and a clean dialysate solution outlet valve 102 for pumping clean dialysate solution to the dialyser 12. The first flow balance pump chamber 100 also has a spent dialysate solution inlet valve 118 for receiving spent dialysate from the dialyser 12 and a spent dialysate solution outlet valve 120 for pumping the spent dialysate to drain via drain outlet port 122.

At any one time, only one of valves 98, 102, 118 or 120 will be open and the other three valves will be closed. The flow balance function, as described above, requires alternating the function of each flow balance pump approximately every 20 cycles. Therefore, when the first flow balance pump 100 is pumping clean dialysate solution to the dialyser 12, only valves 98 and 102 are in use and when the first flow balance pump 100 is pumping spent dialysate solution from the dialyser 12 to drain, only valves 118 and 120 will be in use.

The clean dialysate solution is pumped out of the first flow balance pump chamber 100 through the first flow balance pump clean dialysate solution outlet valve 102, upon closure of the first flow balance pump clean dialysate inlet valve 98, to the dialyser 12 via the dialyser outlet port 104. Prior to passing through the dialyser outlet point 104, the clean dialysate passes through a second dialysate sensor cell 136, also known as a pre-dialyser sensor cell, to characterise the clean dialysate solution. The second dialysate sensor cell 136 is located upstream, preferably immediately upstream, of said outlet point 104. A second clean dialysate sensor cell 136 is provided to corroborate the provided by measurements taken at the first dialysate sensor cell 130 and to ensure that no contamination of the clean dialysate solution has occurred in the flow balance chambers 100, 108.

Spent dialysate solution returns to the cartridge 30 from the dialyser 12 via the dialyser inlet port 106 and flows through a spent dialysate sensor cell 142, also known as a post-dialyser sensor cell. The spent dialysate sensor cell 142 is provided so as to characterise the spent dialysate when it returns to the cartridge 30, this enables the detection of contaminants such as blood which may be present in the dialysate solution after passing through the dialyser 12. Provision of two sensor cells 130, 136 allows a comparison to be made between two locations, i.e. pre and post the dialyser 12, rather than against absolute values.

The second flow balance pump chamber 108 has a spent dialysate solution inlet valve 110 for receiving spent dialysate solution from the dialyser 12 and a spent dialysate solution outlet valve 112 for pumping the spent dialysate solution to drain via drain outlet port 122. The second flow balance pump 108 also has a clean dialysate solution inlet valve 114 for receiving clean dialysate solution from the acid pump chamber 76 and a clean dialysate solution outlet valve 116 for pumping clean dialysate solution to the dialyser 12.

At any one time, only one of valves 110, 112, 114, 116 will be open and the other three valves will be closed. When the second flow balance pump 108 is pumping clean dialysate solution to the dialyser 12, only valves 114 and 116 will be in use and when the second flow balance pump 108 is pumping spent dialysate solution from the dialyser 12 to drain, only valves 114 and 116 will be in use.

In the illustrated example, the operation of the first and second flow balance pumps 100, 108 can be switched so that the first flow balance pump 100 is used to draw spent dialysate solution from the dialyser 12 and the second flow balance pump 108 is used to pump clean dialysate solution into the dialyser 12 as described below.

The clean dialysate solution is drawn into the second flow balance pump chamber 108 from the acid pump 76 via the second flow balance pump clean dialysate solution inlet valve 114 upon actuation of the diaphragm. The clean dialysate solution is then pumped from the second flow balance pump chamber 108 via the second flow balance pump clean dialysate solution outlet valve 116, upon closure of the clean dialysate solution inlet valve 114, to the dialyser 12.

Spent dialysate solution from the dialyser 12 is drawn into the first flow balance pump 100 via the second flow balance pump spent dialysate solution inlet valve 118. The spent dialysate solution is then pumped out of the first flow balance pump chamber 100 via the second flow balance pump spent dialysate solution outlet valve 120, upon closure of the spent dialysate solution inlet valve 118, to drain via drain outlet port 122. Prior to flowing to drain, the spent dialysate solution passes through drain sensor cell 148 located upstream, preferably immediately upstream, of the drain outlet 122. Using various combinations of the valves and pumps it is possible to flow the acid, bicarbonate solution, or purified water through the cartridge 30 without passing through the dialyser 12. Providing a single sensor proximate to the drain valve 122, preferably immediately upstream of said drain valve, then each component, or several of the components combined can be sensed prior to enabling the solution to flow to the dialyser 12. Alternatively, a separate sensor system could be provided for each of the components of the dialysate solution.

The system may be configured to run in a bypass mode periodically, such as hourly, where each of the components will be passed through the cartridge and characterised at 122 so as to check the reference measurements of the system so as to recalibrate the sensing system of the dialysis machine. This removes the dependence of the sensor systems of the machine 10 from dependence on absolute values.

The volume of fluid that is returned from the dialyser 12 is greater than the volume of fluid that is pumped to the dialyser via the first or second flow balance pump 100, 108. The first and second flow balance pumps have fixed volumes meaning that the excess fluid volume cannot be accommodated in the first or second flow balance pump. An ultrafiltration pump 200 is provided between the first and second flow balance pumps 100, 108 and has an inlet valve 202 and an outlet valve 204. The ultrafiltration pump 200 comprises a concave recess in the cartridge closed by a flexible diaphragm, the concave recess and the flexible diaphragm defining an ultrafiltration pump chamber.

In use, the inlet valve 202 of the ultrafiltration pump 200 is opened to allow the ultrafiltration pump 200 to draw in a pre-determined volume of spent dialysate solution. When the inlet valve 202 of the ultrafiltration pump 200 is open, the outlet valve 204 of the ultrafiltration pump 200 is closed. When the ultrafiltration pump 200 has received a volume of spent dialysate solution, the outlet valve 204 is opened and the spent dialysate solution in the ultrafiltration pump chamber is pumped through the outlet valve 204 to drain via the drain outlet port 122. When the outlet valve 204 of the ultrafiltration pump 200 is open, the inlet valve 202 of the ultrafiltration pump 200 is closed.

Regeneration

Figure 4:
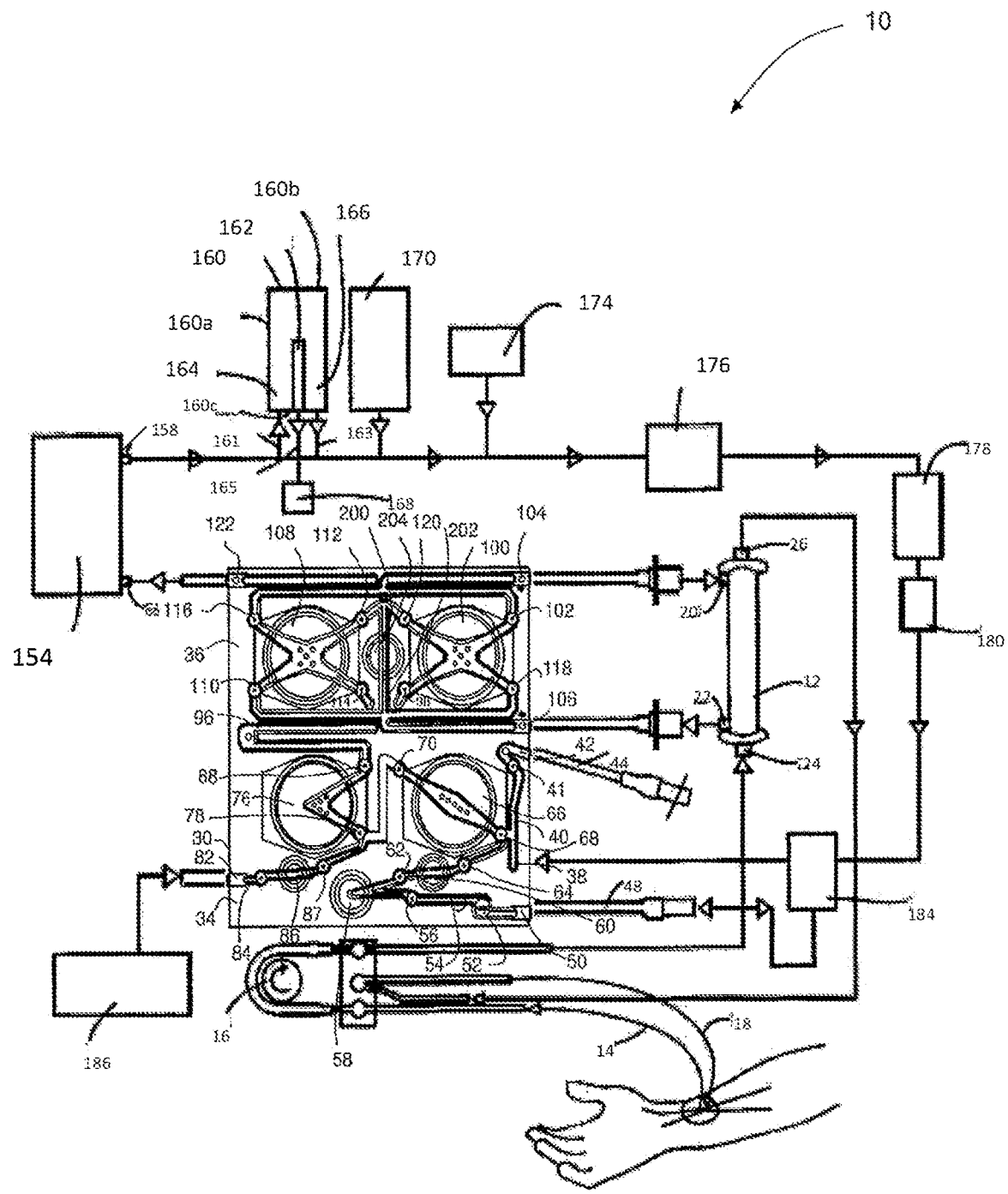
FIG. 4 shows a schematic view of a closed loop recirculating and regenerating dialysis apparatus including the dialysis cartridge of FIG. 2.

In FIG. 1, the spent dialysis is shown as being pumped to drain and therefore discarded. FIG. 4, as described below, illustrates a system for regenerating and recirculating spent dialysis.

At the beginning of a dialysis session, the hemodialysis machine is primed with a known quantity of pre-mixed dialysate solution or purified water via flow input ports 170 or 174. The input port(s) 170, 174 for the pre-mixed dialysate solution and purified water are located at an elevation higher than the highest elevation of the hemodialysis machine.

If purified water is used to prime the hemodialysis machine, the purified water is circulated through the hemodialysis machine prior to connection to the patient to dose the purified water in a known manner by circulating the purified water through a dialysate regeneration device.

Instead of spent dialysate solution being pumped to drain via the drain outlet port 122, FIG. 4 shows that spent dialysate solution is pumped to the dialysate regeneration device cartridge 154 via the drain outlet port 122.

In the illustrated embodiment, the dialysate regeneration device 154 comprises a material, such as sorbent, within a container that has a spent dialysate solution inlet 156 and a clean dialysate solution outlet 158. The spent dialysate solution is pumped through the sorbent to regenerate the spent dialysate solution in a known manner.

"Ultrafiltrate" is intended to mean the waste product which is removed from a patients blood into the dialysate solution during hemodialysis treatment.

The dialysate regeneration device 154 sets the proportion of the base constituent parts, i.e. acid and bicarbonate, in the dialysate solution after removal of ultrafiltrate from the dialysate solution. The clean dialysate solution, after regeneration, is of greater volume in the system than at the beginning of the dialysis session. The excess liquid in the system is removed via an overflow device 162 provided in a reservoir 160.

Sodium bicarbonate is a natural food source for biofilm which can cause bio-incompatibility and unacceptable errors in clean dialysate solution dosing and control. An endotoxin filter 176 is provided downstream of the reservoir 160 for removing biofilm flushed through the clean dialysate solution fluid circuit by the dialysate solution.

The clean dialysate solution having been filtered and potentially stored in the reservoir for a period of time is likely to be at a temperature below that of the human body. A heater 178 may be provided downstream of the endotoxin filter 176 for heating the clean dialysate solution to a temperature of about 37° C. before being passed through an air vent 180 to remove any bubbles from the clean dialysate solution.

The clean dialysate solution passes through the sensor cell 136 which analyses the 'clean' dialysate solution and compares the measurement with earlier measurements to determine the efficiency of the regeneration device by detecting the presence of any contaminants, such as urea, in the dialysate solution. This removes the need for any additional separate sensors.

The acid supply is replaced with a sodium chloride supply 186 for adjusting the clean dialysate solution on each pass of the dialysate solution through the cartridge 30 in accordance with a measurement taken in the sensor cell 136 and by the sensors 52, 54. The acid dosing pump 86 pumps sodium chloride to the acid pump 76 which in turn pumps homogenous, clean dialysate solution to the first flow balance pump 100. The flow balance pumps 100, 108 operate as described previously.

Dialysate Solution Recirculation

In situations where neither filtration equipment nor a continuous purified water supply are available, a single pre-mixed supply of clean dialysate solution 170 can be re-circulated through the hemodialysis machine. By re-circulating the dialysate solution at a comparatively slow speed, i.e. between 100 ml/min and 300 ml/min, configured to saturate the semi-permeable diaphragm of the dialyser 12 with dialysate solution, the dialysate solution remains viable for a number of cycles through the hemodialysis machine. A pre-mixed supply of dialysate solution 170 is provided in a vessel.

In one embodiment, the dialysate solution is circulated through the hemodialysis machine at 100 ml/min and saturates the semi-permeable membrane of the dialyser within one pass of dialysate solution through the hemodialysis machine. The vessel holds a volume of dialysate solution in the order of 60 litres with approximately 25 litres of dialysate solution being circulated through the hemodialysis machine in a single dialysis session.

In another embodiment, the dialysate solution is circulated through the hemodialysis machine at 200 to 300 ml/min and saturates the semi-permeable membrane of the dialyser after a number of passes of dialysate solution through the hemodialysis machine. The vessel holds a volume of pre-mixed dialysate solution in the order of 20 litres for approximately two hours. The dialysate solution is re-circulated through the hemodialysis machine a number of times.

Figure 5:
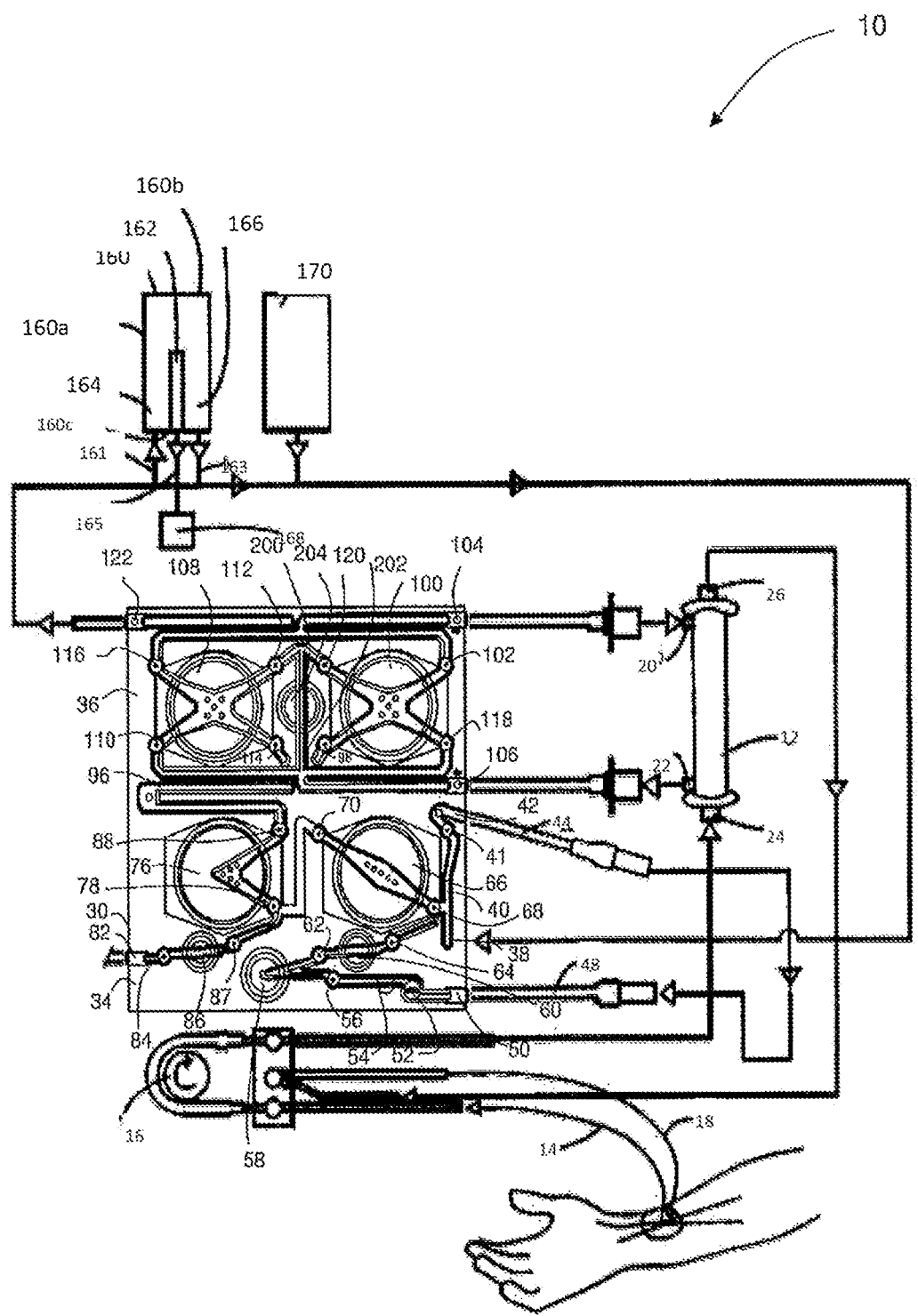
FIG. 5 shows a schematic view of a closed loop recirculating dialysis apparatus including the dialysis cartridge of FIG. 2.

Referring to FIG. 5, the dialysate solution can be re-circulated using the following method:

i) Connecting the drain port 122 to the clean dialysate inlet port 38;

ii) Disconnecting and blocking the acid inlet port 82;

iii) Connecting the water outlet port 42 to the bicarbonate inlet port 50;

iv) Priming the hemodialysis machine with pre-mixed clean dialysate solution and purified water;

v) Connecting the clean dialysate outlet port to the inlet of the dialyser;

vi) Connecting the outlet of the dialyser to the spent dialysate solution inlet port and, v) Flowing dialysate solution through the hemodialysis machine 10 at a fluid flow rate configured to saturate the semi-permeable diaphragm of the dialyser 12.

The reservoir, as described with reference to FIG. 5, takes ultrafiltrate generated during a dialysis session and removes it from the system via the reservoir overflow device 162 to the reservoir drain 168.

Structure of the Sensor Cells

Figure 6:
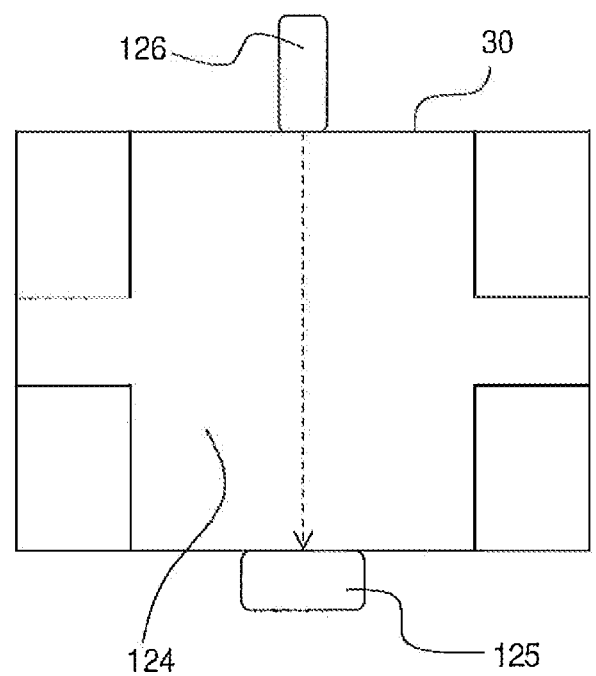
FIG. 6 shows a schematic cross-sectional view of a sensor system for use in an embodiment of the invention.

Referring to FIG. 6, which illustrates sensor cell 124 as an example, each sensor cell forms part of an optical sensor system along with a corresponding a detector 125 and a light source 126. The sensor cells 124 are provided on the cartridge 30 in the form of a chamber along the fluid pathway of the dialysate solution. The walls of the sensors cells 124 on the door side 32 and platen side 31 of the cartridge 30 are selected so as to provide the best transmittance of an optical signal from the light source 126 therethrough.

In the illustrated embodiment, both the platen and door sides of the sensor cell 124 include a window, e.g. an aperture, in the cartridge 30, that is covered in a clear flexible membrane. The sensor cell membrane may be formed from the same material as the membrane and may be formed from the same membrane that covers the flow chambers, although, in alternative arrangements, the membrane may be separate from the membrane and/or may be a different material thereto. The membrane of the sensor cells is able to be secured to the platen by use of a vacuum so as to provide a flat surface which works to provide a uniform transmission of the optical signal and minimises reflectance of the signal. Similarly, the membrane of the sensor cells is able to be secured to the door by use of a vacuum. Use of a different material for the platen and door sides of the sensor cells to the material used to produce the cartridge 30 reduces the amount of attenuation of the optical signal, which occurs when passing through the cartridge material.

The light for each of the sensor systems of the dialysis machine is provided from a single light source which is split off, e.g. by the use of optical fibres, to direct the optical signal to each of the sensor systems. This enables the light source, i.e. the emission spectra, of the light source for each sensor system to be identical. In alternative arrangements, the light source of each sensor system may be separate components, such as LEDs, which are able to produce a very reproducible emission spectra.

The detector 125 is in the form an optical spectrometer, located in the platen of the main body 2 of the dialysis machine 10, and the light source 126 is provided in the door 4 of the dialysis machine. The detector 125 and light source 126 are arranged so as to oppose each other and have a sensor cell 124 positioned therebetween, as is shown in FIG. 6. It will be appreciated that the light source 126 may alternatively be provided in the platen of the main body 2 and the detector may be provided in the door 4. The detector receives the light signal which has passed from the light source, through the cell 124 and through the dialysate flowing through the cell. The received signal is passed to a processor, such as a microprocessor, which determines characteristics of the dialysate based upon the light frequencies absorbed by the dialysate. By analysing the received signal spectroscopically and comparing it to the known sent light signal various parameters, such as the concentrations of dialysate, acid, sodium bicarbonate and water in their respective flow paths can be determined. Furthermore, this machine is able to determine if there is a blood leak in any of the flow paths.

Additionally, providing sensors on both the clean dialysate and spent dialysate lines ensures that the system does not need to take regular background light readings as any background light that is present in the readings will simply be eliminated by virtue of the comparison when the readings are compared.

Figure 7:
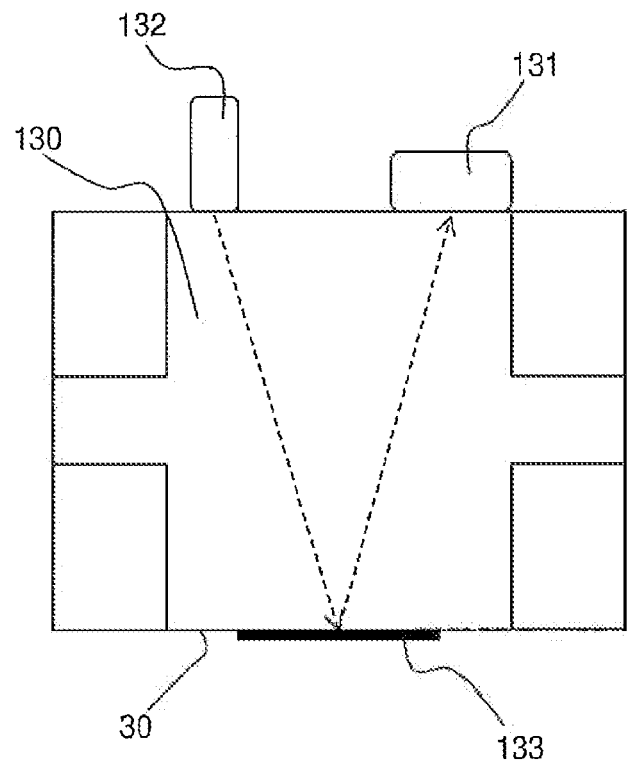
FIG. 7 shows a schematic cross-sectional view of an alternative sensor system for use in an embodiment of the invention.

With reference to FIG. 7, an alternative sensor system is discussed with reference to sensor cell 130 as an example. As is illustrated, both the detector 131 and the light source 132 are provided on the same side of the cartridge 30. This arrangement utilises reflectance spectroscopy and uses a reflective surface 133 so as to reflect the light source back through the sensor cell 130, which works to double the absorption of the light by the solution, thus increasing the sensitivity of the sensor system. The reflective surface 133 may be formed as a part of the membrane (e.g. an interior or exterior surface of the membrane), as illustrated. Alternatively, the reflective surface may be provided on the platen or the door 4. In a further alternative arrangement, the sensor cell may be provided with multiple reflective surfaces to reflect the light through the sensor cell multiple times, further to increase the absorbance and thus the sensitivity of the sensor system.

The light frequency used may be ultra violet, visible light or near infrared. Instead of light absorption or reflectance, characteristics of the fluid may be determined from measuring its refractive index.

It will be appreciated that although the structure of the sensor systems of FIGS. 6 and 7 has been discussed with reference to sensor cells 124 and 130, respectively, these have been used as examples only. All of the sensor cells on the cartridge may be provided as described with reference to FIG. 6 or FIG. 7, or a mixture of sensor systems may be provided in a single dialysis system.

In embodiments including refraction spectroscopy or ultrasonic sensing, the measurements recorded by the sensor cells may use the measurements taken by the temperature sensor 52 temperature readings further to increase the accuracy of the systems and account for changes in the refractive index or the speed of sound through a medium which occur due to changes in temperature.

The morphology of the cartridge may be modified so as further to increase the sensitivity of the sensor systems. A structure may be provided so as to collimate the light from the source, which can help to improve resolution. Alternatively, a structure, e.g a raised smooth, curved surface may be provided to amplify any changes in the signal produced by changes in the dialysate, e.g. an optical lever may be provided within the sensor cell.

In a further alternative arrangement, the window(s) of the sensor cell may be covered by a plastics material which is separate from and secured to, e.g. by welding, the cartridge.

It some embodiments, the system may have different pairs of sensors. i.e. transmission, reflectance, ultrasonic, and these could all be used to check against the others.

Each of the sensor cells may further be provided with a coating on at least one surface, where the coating is an active substance designed to emit a measurable characteristic upon interaction with a component of the dialysate solution. Such an active coating could be designed to fluoresce upon interaction with Oxygen, which would allow the sensor systems to monitor proper de-aeration of the dialysate solution.

The dialysis system may further be provided with a sensor for sensing any particulate matter present in the dialysate solution. For example an additional flow cell may be provided for such a measurement. In one embodiment, the sensing could be done using dynamic light scattering so as to sense the distribution of any particulate matter In the embodiments described above, the sensor systems are configured to provide continuous measurement of the dialysate solution, this enables the system to provide immediate feedback if the dialysate solution is found to be contaminated, e.g. by urea or blood in the solution. However, the sensor may alternatively be configured periodically to sense the solutions.

The invention claimed is:

1. A hemodialysis machine comprising:
   a removable, mountable cartridge, a fluid pathway for delivering a dialysate solution, wherein the fluid pathway comprises a pre-dialysis pathway and a post-dialysis pathway; and wherein the cartridge defines the fluid pathway;
   a dialyser for dialysing patient's blood using the dialysate solution, the dialyser connected between the pre-dialysis pathway and the post-dialysis pathway;
   a first sensor system configured to sense a characteristic of the dialysate solution at a first location on the pre-dialysis pathway;

a second sensor system configured to sense a characteristic of the dialysate solution at a second location on the post-dialysis pathway, wherein:
the first sensor system comprises a first sensor cell located on the cartridge and
the second sensor system comprises a second sensor cell located on the cartridge, and
each sensor cell comprises at least one window formed in the cartridge through which a respective detector of each sensor system determines the characteristic of the dialysate solution;
and
a control system configured to make a comparative analysis of the measurements taken by the first sensor system and the second sensor system for monitoring the composition of the dialysate solution, wherein the window comprises a flexible membrane secured to the cartridge.

2. A hemodialysis machine according to claim 1, wherein the cartridge comprises a dialyser outlet and the first sensor cell is located immediately upstream of said dialyser outlet.

3. A hemodialysis machine according to claim 1, wherein the cartridge comprises a dialyser inlet and the second sensor cell is located immediately downstream of said dialyser inlet.

4. A hemodialysis machine according to claim 1, wherein each of the first and second sensor systems senses a characteristic of the dialysate solution by passing light through the solution.

5. A hemodialysis machine according to claim 1, wherein each of the first and second sensor systems senses a characteristic of the dialysate solution by passing ultrasound through the solution.

6. A hemodialysis machine of claim 1, wherein the cartridge comprises a cartridge drain outlet and a third sensor system comprising a third sensor cell located immediately upstream of the cartridge drain outlet.

7. A hemodialysis machine of claim 1, wherein the cartridge comprises a water inlet port and a fourth sensor system comprising a fourth cell located immediately downstream of the water inlet port.

8. A hemodialysis machine according to claim 1, wherein the window comprises a separate plastics material secured to the cartridge.

9. A hemodialysis machine of claim 1, comprising a platen and a door, wherein the cartridge is configured to be removably mountable between said platen and door, the door being capable of opening and closing relative to the platen so as to prevent any external light from entering the sensor cells.

10. A hemodialysis machine according to claim 9, wherein the flexible membrane is coupled to the platen by a vacuum.

11. A hemodialysis machine according to claim 9, wherein the flexible membrane is coupled to the door by a vacuum.

12. A hemodialysis machine according to claim 9, wherein each sensor system comprises a light source and a detector, and wherein each detector is located in the platen.

13. A hemodialysis machine according to claim 12, wherein the light source is located in the door.

14. A hemodialysis machine according to claim 12, wherein the light source is located in the platen.

15. A hemodialysis machine according to claim 14, wherein each sensor system comprises a reflective surface.

16. A hemodialysis machine according to claim 15, wherein the reflective surface is provided on the door.

17. A hemodialysis machine according to claim 12, further comprising an optical lever.

18. A hemodialysis machine according to claim 17, wherein the optical lever is formed integrally with the cartridge.

19. A hemodialysis machine according to claim 1, wherein at least one of the sensor cells comprises a functional coating configured to react to the dialysate solution.

20. A hemodialysis machine according to claim 1, further comprising a particulate sensor configured to analyse the size distribution of particulate matter in the dialysate.

21. A hemodialysis machine according to claim 1, further comprising a fixed volume of dialysate solution.

22. A hemodialysis machine according to claim 1, wherein the cartridge is disposable.

23. A hemodialysis machine according to claim 1, further comprising an additional sensor system arranged to sense an additional characteristic of the dialysate solution, the additional sensor system being arranged to sense one or more from temperature, conductivity or pH of the solution.

24. A hemodialysis machine according to claim 9, wherein each sensor system comprises a light source and a detector.

25. A hemodialysis machine according to claim 24, wherein each light source and each detector are located outside and immediately adjacent the at least one window of each respective sensor cell, such that light is directly transmitted by each light source into a respective sensor cell and directly received by each detector after passing through fluid in a respective sensor cell at least once.

26. A hemodialysis machine according to claim 25, wherein the window comprises a flexible membrane secured to the cartridge, the flexible membrane is coupled to the platen by a vacuum, each detector is located in the platen adjacent the flexible membrane.

27. A hemodialysis machine according to claim 26, wherein each light source is located in the door such that, upon closing of the door, the light source is arranged opposite to the detector to receive light from the light source after passing through fluid in each sensor cell.

28. A hemodialysis machine according to claim 25, wherein: the window comprises a flexible membrane secured to the cartridge, the flexible membrane is coupled to the platen by a vacuum, and each light source is located in the platen adjacent flexible membrane.

29. A hemodialysis machine according to claim 28, wherein each detector is located in the door such that, upon closing of the door, the detector is arranged opposite to the light source to receive light from the light source after passing through fluid in each sensor cell.

30. A hemodialysis machine according to claim 25, wherein:
the window comprises a flexible membrane secured to the cartridge, the flexible membrane is coupled to the platen by a vacuum, a reflective surface contained in the door is arranged adjacent each sensor cell, and each detector and each light source is located in the platen adjacent flexible membrane such that, light emanating from the light source is reflected off the reflective surface and received by the detector.

31. A hemodialysis machine according to claim 25, wherein:
the window comprises a flexible membrane secured to the cartridge, the flexible membrane is coupled to the door by a vacuum, a reflective surface contained in the door is arranged adjacent each sensor cell, and each detector and each light source is located in the door adjacent flexible membrane such that, light emanating from the light source is reflected off the reflective surface and received by the detector.

\* \* \* \* \*